US00PP15354P2

(12) United States Plant Patent
Bradford

(10) Patent No.: US PP15,354 P2
(45) Date of Patent: Nov. 23, 2004

(54) APRICOT TREE 'GOLDENBLUSH'

(50) Latin Name: *Prunus armeniaca*
Varietal Denomination: Goldenblush

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/746,713

(22) Filed: Dec. 29, 2003

(51) Int. Cl.[7] ..... A01H 5/00
(52) U.S. Cl. ..... Plt./186
(58) Field of Search ..... Plt./186

(56) References Cited

U.S. PATENT DOCUMENTS

PP8,932 P 10/1994 Bradford et al.

OTHER PUBLICATIONS

UPOV–ROM Plant Variety Database,hit on peach 'Golden Blush', 2004/02.*

* cited by examiner

*Primary Examiner*—Anne Marie Grunberg

(57) ABSTRACT

The present invention relates to an apricot tree, *Prunus armeniaca,* and more particularly to a new and distinct variety broadly characterized by a medium size, vigorous, half-hardy, and medium productive tree. Being self-unfruitful, the present variety requires cross pollinization from another early blooming apricot. The fruit matures under the ecological conditions described during the first week in June, with first picking on Jun. 2, 2003. The fruit is medium in size, orange yellow with a red blush in skin color, freestone in type, orange yellow in flesh color, very firm in texture, and sweet in flavor. The variety is a second generation seedling having 'Goldensweet' (U.S. Plant Pat. No. 8,932) apricot as the selected seed grandparent and an unnamed seedling as the selected pollen grandparent.

1 Drawing Sheet

Botanical classification: *Prunus armeniaca.*
Variety denomination: 'Goldenblush'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of apricot tree, which has been denominated varietally as 'Goldenblush'.

During the spring of 1994 I gathered open pollinated seeds from an unnamed apricot seedling in my experimental orchard near Le Grand, Calif. in Merced County (San Joaquin Valley). That unnamed seedling was a first generation cross using 'Goldensweet' (U.S. Plant Pat. No. 8,932) apricot tree as the selected seed parent and another unnamed seedling as the selected pollen parent. The seeds of the present cross were then germinated and grown as seedlings on their own root in my greenhouse. Upon reaching dormancy that fall, the seedlings were transplanted as a group to a cultivated area of my experimental orchard described above. During the 1998 evaluation season, I selected the present variety as a single tree from the group of seedlings described above because the fruit was early in maturing, firm, sweet, and cosmetically attractive. Subsequent to origination of the present apricot tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed grandparent, 'Goldensweet' (U.S. Plant Pat. No. 8,932), by producing fruit that is somewhat oblong in shape, medium in size, firm in texture, sweet in flavor, and freestone in type, but is distinguished therefrom by blooming about ten days earlier, by being self-unfruitful, and by producing fruit that has a much higher degree of red blush in the skin color and that matures about fourteen days earlier.

SUMMARY OF VARIETY

The present apricot variety is characterized by a medium size, vigorous, half-hardy, and medium productive tree. Being self-unfruitful, the present variety requires cross pollinization from another early blooming apricot. The fruit matures under the ecological conditions described during the first week in June, with first picking on Jun. 2, 2003. The fruit is medium in size, orange yellow with a red blush in skin color, freestone in type, orange yellow in flesh color, very firm in texture, and sweet in flavor.

DRAWING

The accompanying photograph exhibits four whole fruits positioned to display the characteristics of the skin color and form, one fruit divided around the suture plane to reveal the flesh and stone, and typical leaves.

DETAILED BOTANICAL DESCRIPTION

Referring now more specifically to the pomological characteristics of this new and distinct apricot tree, the following has been observed under the ecological conditions prevailing near Le Grand, Merced County (San Joaquin Valley), Calif., and was developed at the state of shipping ripe on Jun. 5, 2003, on the original tree during its ninth growing season. All major color code designations are by reference to the Inter-Society Color Council, National Bureau of Standards. Common color names are also used occasionally.

TREE

Size: Medium, reaching and maintaining a height of 12' [3.7 m.] and a spread of 8' [2.4 m.] after nine growing seasons utilizing typical dormant pruning.

Vigor: Medium, responding typically to irrigation and fertilization. The variety grows about 3' [0.9 m.] of surplus top-growth during the spring and summer. The plant should be grown on a standard commercial rootstock for production purposes.

Growth: Upright and open.

Form: Trained to a central leader shape by pruning.

Hardiness: Hardy with respect to central California winters.

Heat Tolerance: Observed to perform adequately in typical central California climatic conditions, which typically include prolonged periods of heat.

Drought tolerance: Variety is developed for commercial orchards and requires regular irrigation.

Production: Medium productive.

Fertility: Self-unfruitful, requiring cross pollination by another suitable early blooming apricot. The variety was pollinated by '12P515' (unpatented) apricot in 2003.

Bearing: Uncertain bearer, very dependent on warm weather during the blooming season, susceptible to frost during the bloom.

Trunk:

*Size.*—Medium, reaching a maximum diameter of 3¾" [95 mm.] after the ninth growing season.

*Texture.*—Shaggy.

*Bark color.*—Dark grayish brown [62. d.gy.Br] with Moderate orange yellow [71. m.OY] variegation.

*Lenticels.*—Approximate Number Per Square Inch: 15. Color: Light grayish yellowish brown [79. l.gy.yBr]. Typical Size: ⅛" to ⅜" [3.2–9.5 mm.].

Branches:

*Size.*—Diameter of first side limb is 1⅝" [41 mm.] measured 12" from the central leader, typical of *Prunus armeniaca*, and dependent upon cultural practices and climatic conditions.

*Texture.*—Smooth on first year wood, increasing roughness with age.

*Color.*—1st Year Wood Topside: Deep red [13. deep R]. 1st Year Wood Underside: Light yellow green [119. l.YG]. Older Wood: Dark reddish brown [44. d.rBr].

*Lenticels.*—Approximate Number Per Square Inch: 80. Color: Light orange yellow [70. l.OY]. Typical size: 1/64" to ⅛" [0.4–3.2 mm.].

Leaves:

*Size.*—Medium. Average Length: 3¼" [83 mm.]. Average width: 2¾" [70 mm.].

*Arrangement.*—Alternate.

*Thickness.*—Medium.

*Form.*—Orbicular to oval.

*Apex.*—Acuminate.

*Base.*—Some rounded and some cuneate.

*Surface.*—Smooth.

*Color.*—Dorsal Surface: Deep yellow green [118. deep YG]. Ventral Surface: Strong yellow green [117. s.YG].

*Margin.*—Finely serrate.

*Venation.*—Pinnately net veined.

*Petiole.*—Average Length: 1¼" [31.8 mm]. Average Thickness: 1/16" [1.6 mm.]. Color: Moderate yellow green [120. m.YG] on the bottom side and Moderate red [15. m.R] on the topside.

*Stipules.*—Number: Typically 2 primary and up to 6 secondary per young emerging leaf. Primary length: ¼" [6.4 mm.]. Color: Moderate red [15. m.R], darker if in direct sunlight.

*Glands.*—Number: Usually 2, sometimes 4. Position: Usually occurring in alternately positioned pairs on the petiole, with one pair typically ⅜" [9.5 mm.] below the blade. Size: Small. Form: Globose. Color: Dark grayish red [20. d.gy.R].

*Leaf buds.*—Conic, medium size.

Flower buds:

*Hardiness.*—Half-hardy, with respect to central California winters.

*Diameter.*—Typically ¼" [6.4 mm.] 5 days before bloom.

*Length.*—Typically ⅜" [9.5 mm.] 5 days before bloom.

*Form.*—Not appressed.

*Surface.*—Pubescent.

*Color.*—Light purplish pink [249. l.pPk].

Flowers: Perfect, complete, perigynous, usually a single pistil, typically twenty-four or more stamens, five sepals and petal locations alternately positioned.

*Average flower diameter.*—1 7/16" [36.5 mm.].

*Number of petals.*—Usually five.

*Petal shape.*—Circular to elliptical.

*Petal margin.*—Wavy.

*Average petal diameter.*—⅝" [15.9 mm.].

*Average petal length.*—9/16" [14.3 mm.].

*Petal apex.*—Rounded.

*Petal base.*—Rounded.

*Petal color.*—Pale purplish pink [252. p.pPk].

*Anther color.*—Light yellow [86. l.Y].

*Stigma color.*—Pale greenish yellow [104. p.gY].

*Sepal color.*—Deep red [13. deep R].

*Sepal length.*—7/32" [5.6 mm.].

*Sepal width.*—3/16" [4.8 mm.].

*Average pistil length.*—½" [12.7 mm.].

*Average stamen length.*—7/16" [11.1 mm.].

*Fragrance.*—Moderate.

*Pollen production.*—Abundant.

*Blooming period.*—Early compared to other apricots, about ten days before 'Goldensweet' (U.S. Plant Pat. No. 8,932).

*Onset of bloom.*—One percent on Feb. 13, 2003.

*Date of full bloom.*—Feb. 22, 2003.

*Duration of bloom.*—One to two weeks, dependent on ambient temperature.

*Number per cluster.*—Up to 3 with mostly singles.

FRUIT

Maturity when described: Shipping ripe, Jun. 5, 2003.

Date of first picking: Jun. 2, 2003.

Date of last picking: Jun. 10, 2003.

Size: Uniform, medium.

*Average diameter axially.*—2⅛" [54.0 mm.].

*Average diameter across suture plane.*—2" [50.8 mm.].

*Typical weight.*—2.9 ounces [82 grams].

Form: Uniform, symmetrical, slightly oblong and compressed laterally.

*Longitudinal section form.*—Oval.

*Transverse section through diameter.*—Elliptical.

Suture: A distinct groove extending from the base to the apex, some stitching and some deep crevices usually near the apex or the stem cavity.

Ventral surface: Rounded, lipped throughout on both sides.

Lips: Equal.

Cavity: Flaring, circular to somewhat elongated in the suture plane, suture showing on one side.

*Depth.*—5/16" [7.9 mm].
*Breadth.*—5/8" [15.9 mm.].
Base: Somewhat truncate.
Apex: Rounded.
Pistil point: Apical, negligible in length.
Stem: Medium.
*Average length.*—5/16" [7.9 mm.].
*Average width.*—1/16" [1.6 mm.].
Skin:
*Thickness.*—Medium.
*Surface.*—Smooth.
*Tenacity.*—Tenacious to flesh.
*Astringency.*—Slightly astringent.
*Tendency to crack.*—Slight in wet season.
*Color.*—About 40 percent Deep reddish orange [36. deep rO] smoothly blending into a Brilliant orange yellow [67. brill.OY] background.
Flesh:
*Color.*—Light orange yellow [70. l.OY] to Brilliant orange yellow [67. brill.OY] with increasing maturity.
*Surface of pit cavity.*—Covered with Light orange yellow [70. l.OY] fibers.
*Amygdalin.*—Moderate.
*Juice.*—Abundant, rich.
*Texture.*—Very firm, meaty.
*Fibers.*—Abundant, moderately coarse.
*Ripens.*—Slightly earliest along the apex.
*Flavor.*—A tasty balance of acid and sugar, typically 17 brix.
*Aroma.*—Slight.
*Eating quality.*—Very good.

STONE

Type: Freestone.
Form: Oval.
Hilum: Narrow, oblong.
Base: Rounded, cupped at the hilum.
Apex: Cuneate with an average angle of 100 degrees.
Sides: Equal.
Surface: Rough.
External color of stone: Light yellowish brown [76. l.yBr].
Pit wall color when cracked: Pale orange yellow [73. pOY].
Cavity surface color: Light grayish yellowish brown [79. l.gy.yBr].
Average pit wall thickness: 1/16" [1.6 mm.].
Average width: 15/16" [23.8 mm.].
Average length: 1 5/16" [33.3 mm.].
Average breadth: 7/16" [11.1 mm.].
Tendency to split: Slight.
Kernel:
*Form.*—Oval.
*Pellicle color.*—Strong yellowish brown [74. s.yBr].
*Skin color.*—Pale orange yellow [73. p.OY] when first cracked and Dark orange yellow [72. d.OY] when dry.
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of apricot tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of apricot tree, substantially as illustrated and described, that is similar to its selected seed grandparent, 'Goldensweet' (U.S. Plant Pat. No. 8,932), by producing fruit that is somewhat oblong in shape, medium in size, firm in texture, sweet in flavor, and freestone in type, but is distinguished therefrom by blooming about ten days earlier, by being self-unfruitful, and by producing fruit that has a much higher degree of red blush in the skin color and that matures about fourteen days earlier.

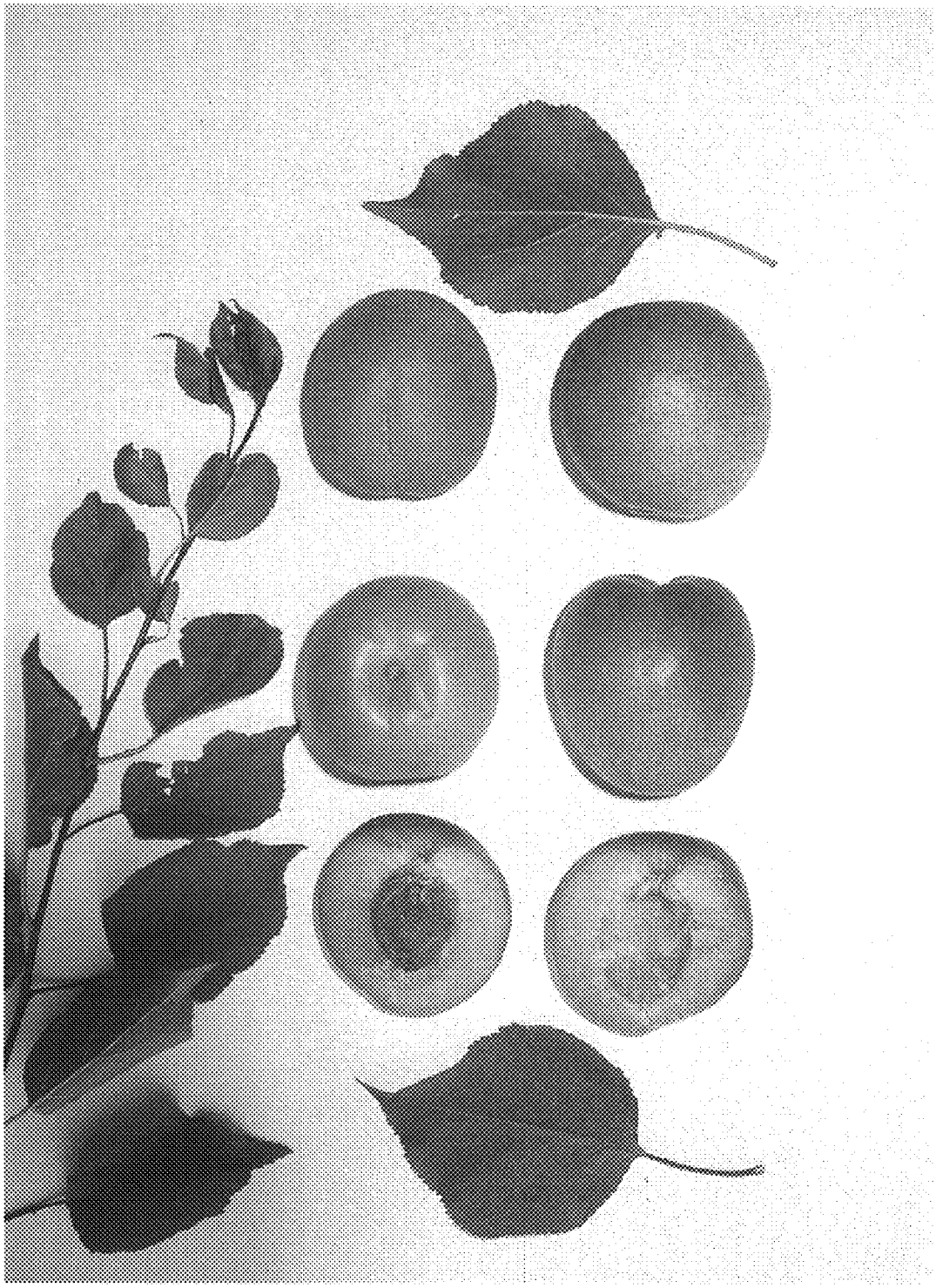

* * * * *